United States Patent [19]

Teisseire

[11] Patent Number: 5,021,425

[45] Date of Patent: Jun. 4, 1991

[54] USE OF 2-AZABICYCLOI[2.2.2]OCTANE-3-CARBOXYLIC ACID DERIVATIVES FOR THE TREATMENT OF ARTERITIS

[75] Inventor: Bernard Teisseire, Paris, France

[73] Assignee: Adir et Compagnie, Neuilly-sur-Seine, France

[21] Appl. No.: 396,864

[22] Filed: Aug. 22, 1989

[30] Foreign Application Priority Data

Aug. 24, 1988 [FR] France .................................. 88 11157

[51] Int. Cl.⁵ ............................................ A01N 43/42
[52] U.S. Cl. .................................... 514/299; 540/477; 546/112
[58] Field of Search ...................... 514/299, 411, 235.8; 546/112; 540/477

[56] References Cited

U.S. PATENT DOCUMENTS 4,397,857 8/1983 Vincent et al. ...................... 514/299

OTHER PUBLICATIONS

Ondetti, Science, vol. 196, pp. 441–443, 1977.
Schölkens et al., Arzneim–Forsch. Drug Research 34(II), 190 10b, pp. 1417–1425, 1984.
Unger et al., Arzneim–Forsch.-Drug Research, 34II, 10b, pp. 1426–1430, 1984.

Primary Examiner—Jose G. Dees
Assistant Examiner—Deborah D. Carr
Attorney, Agent, or Firm—Gordon W. Hueschen

[57] ABSTRACT

Use of 2-azabicyclo[2.2.2.]octane-3-carboxylic acid derivatives and their salts for the treatment of arteritis and more especially arteritis of the lower limbs, disorders of the cerebral circulation and more especially disorders of cerebral senescence and migraine, and disorders of vision such as retinal disorders of vascular origin, diabetic retinopathy, chorioretinal atrophy and chorioretinal degeneration.

6 Claims, No Drawings

USE OF 2-AZABICYCLO[2.2.2]OCTANE-3-CARBOXYLIC ACID DERIVATIVES FOR THE TREATMENT OF ARTERITIS

The present invention relates to the use of 2-azabicyclo[2.2.2]octane-3-carboxylic acid derivatives treatment of vascular diseases.

More specifically, the invention relates to the use for the treatment of diseases resulting from impairment of the vascular wall or of disorders of the microcirculation, of derivatives of general formula (I):

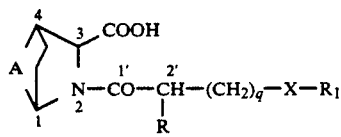

in which
A denotes a vinylene or dimethylene radical,
q is 0 or 1,
R denotes a lower alkyl radical which can bear an amino group,
X denotes —S— and $R_1$ denotes H, or alternatively X denotes —NH— and
$R_1$ denotes a hydrogen atom or a radical of formula:

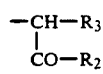

$R_2$ denotes a hydroxyl or a lower alkoxy group,
$R_3$ denotes a hydrogen atom, a linear or branched alkyl, cycloalkyl or phenylalkyl radical having not more than 8 carbon atoms in all, or a radical of formula:

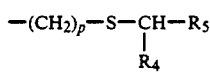

in which:
$R_4$ is H or a lower alkyl or ($C_3$ to $C_6$)cycloalkyl radical,
$R_5$ is H or a ($C_3$ to $C_6$)cycloalkyl or (lower alkoxy)-carbonyl radical, and
p is 1 or 2,
on the understanding that lower alkyl or alkoxy radical denotes groups having from 1 to 4 carbon atoms, as well as their addition salts obtained with a therapeutically compatible inorganic or organic base or with a therapeutically compatible inorganic or organic acid when X denotes NH.

As a base capable of salifying the compounds of formula (I), sodium hydroxide, potassium hydroxide, calcium hydroxide or aluminum hydroxide, alkali metal or alkaline-earth metal carbonates or organic bases such as triethylamine, benzylamine, diethanolamine, tert-butylamine, dicyclohexylamine, arginine, and the like, may be used.

Among acids which can be added to the compounds of formula (I) to obtain an addition salt, hydrochloric, sulfuric, phosphoric, tartaric, malic, maleic, fumaric, oxalic, methanesulfonic, ethanesulfonic, camphoric and citric acids, and the like, may be mentioned without implied limitation.

The compounds of formula (I) contain at least two asymmetric carbon atoms. The use according to the invention can relate to the different isomers of the derivatives of formula (I), isolated or even as a mixture. However, the use according to the invention relates preferentially to the derivatives of formula (I) in which the asymmetric carbon atoms have the S configuration.

The compounds of formula (I) which are preferentially usable according to the invention are those for which:
A denotes a dimethylene group,
q is 0,
R denotes a methyl or 4-aminobutyl group,
X denotes NH, and
$R_1$ denotes a radical of formula:

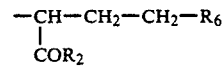

$R_2$ possessing the definition stated above,
$R_6$ denoting a methyl, ethyl or phenyl group, as well as their addition salts.

Among the latter, that for which $R_2$ denotes ethoxy and $R_6$ is a phenyl radical, and R denotes a methyl group, is preferred. The compound in question is (S,S,S)-2-{2-[3-phenyl-1-(ethoxycarbonyl)-propylamino]propionyl}-3-carboxy-2-azabicyclo[2.2.2]octane.

The compounds of the formula (I) are described in European Patent 0,051,020, as well as in European Patent Application 0,105,102, as being usable in the treatment of arterial hypertension at dosages of between 1 and 200 mg.

The Applicant has now discovered that the products of formula (I) possess advantageous properties, applicable for the treatment of diseases due to an impairment of the vascular wall, as well as for the treatment of diseases resulting from disorders of the microcirculation, and at doses not giving rise to antihypertensive activity.

Among the conditions capable of being treated by the medicinal products obtained according to the invention, arteritis, arteritis of the lower limbs, and also disorders of the cerebral circulation and especially disorders of cerebral senescence and migraine, and disorders of vision such as retinal disorders of vascular origin, diabetic retinopathy, chorioretinal atrophy and chorioretinal degeneration should be mentioned.

The medicinal products intended for the treatment of diseases resulting from impairment of the vascular wall as well as for disorders of the microcirculation, obtained using, according to the invention, the compounds of formula (I) or their pharmaceutically acceptable salts, will be presented in pharmaceutical dosage forms suitable for oral, parenteral and, in particular, intravenous, per- or transcutaneous, nasal, rectal, perlingual, ocular or respiratory administration, and in particular injectable preparations, aerosols, eye or nose drops, tablets, sublingual tablets, sublingual preparations, hard gelatin capsules, capsules, pills, suppositories, creams, ointments, skin gels, and the like.

The dosage varies according to the patient's age and weight, the administration route and the nature of the therapeutic indication and of associated treatments, and ranges from 0.001 mg to 10 mg per dose or per application.

The examples which follow illustrate the invention and in no way limit the latter.

EXAMPLE 1: ACTIVITY OF THE PRODUCTS OF FORMULA (I) AT NON-HYPOTENSIVE DOSES ON PLASMA CONVERTING ENZYME

The use of a derivative of formula (I) — having converting enzyme inhibitory properties — in the treatment of diseases resulting from impairment of the vascular wall as well as for disorders of the microcirculation, presupposes that this product is active with respect to converting enzyme at non-hypotensive doses.

A study was hence carried out on Sprague-Dawley rats weighing from 80 to 100 grams. This group of animals received a product of formula (I) in the drinking water on the basis of 0.1 mg.kg$^{-1}$; another group of animals was not treated. After 7 days of treatment, the rats are anesthetized with 50 mg.kg$^{-1}$ of pentobarbital sodium. A catheter is introduced into the carotid for the collection of two samples, one in a dry tube for assay of the converting enzyme activity, the other on EDTA for the assay of angiotensin I. After collection, the samples are immediately centrifuged at 4° C. and 3,000 rpm for 10 minutes. The supernatants are withdrawn and frozen at −80° C. while awaiting assay. The outcome of the study is that 7 days' oral administration of the product of formula (I) at 0.1 mg.kg$^{-1}$/day led to a 52% inhibition of the circulating enzyme. This result demonstrates that the products of formula (I) act on converting enzyme at non-hypotensive doses.

EXAMPLE 2: DEMONSTRATION OF THE EXISTENCE INSIDE THE VASCULAR WALL OF A RENIN-ANGIOTENSIN SYSTEM SENSITIVE TO THE PRODUCTS OF FORMULA (I)

The experiment was carried out on the femoral and internal saphenous arteries and the saphenous vein of pigs. Minipigs (Charles-River) were anesthetized by an intramuscular injection of 1.5 mg.kg$^{-1}$ of Stresnil and an intraperitoneal injection of pentobarbital sodium (40 mg.kg$^{-1}$), and drained of their blood.

After being collected, the blood vessels were cleared of adherent connective tissue and cut into segments approximately 4 mm long, and were stored in modified Krebs-Ringer bicarbonate medium.

The isometric tension was measured with a tensiometer indicator (Gould UC$_2$) connected to a recorder (Gould). The vascular segments were brought to the optimal point of their length/tension ratio by repeated stimulations with 40 mM KCl.

The vessel segments were left to stand for the purpose of equilibration of the preparation for 45 minutes before the beginning of each experiment. The vascular endothelium was removed from some samples by gently rubbing the surface of the intima using a small forceps.

It was shown that angiotensinogen, angiotensin I ($1.10^{-10}$, $3.10^{-7}$ M) and angiotensin II ($10^{-10}$, $10^{-7}$ M) induced contractions of the femoral arteries. These contractions are dependent on the presence of the endothelium for angiotensinogen and angiotensin I; a complete renin-angiotensin system is hence present in the vascular wall.

It was also shown that products of formula (I) act essentially on the converting enzymes present in the vascular endothelium, thereby demonstrating that the products of formula (I) are capable of being used in the production of medicinal products intended for the treatment of disorders affecting this vascular wall.

EXAMPLE 3: ACTIVITY OF THE PRODUCTS OF FORMULA (I) WITH RESPECT TO AN ISCHEMIC MICROCIRCULATION

The experimental study was carried out on the cremaster muscles of male rats (Sprague-Dawley) after ligation of the common iliac artery.

The muscles were placed in a transparent chamber and perfused with bicarbonate buffer solution equilibrated with a 5:95% $CO_2/N_2$ gaseous mixture. The velocity of the red cells and the diameter of the first or second order arterioles irrigating the cremaster were measured, and the arteriolar blood flow was calculated. Identical data were obtained for four types of venules.

The same types of measurement were performed simultaneously:

on the cremaster perfused normally, on the ligated cremaster, that is to say the cremaster rendered ischemic 2, 7, 14 and 21 days after ligation.

Two groups of animals were studied:

an untreated control group, a group treated orally with a product of formula (I), on the basis of 0.1 mg.kg$^{-1}$ per day.

No difference was observed in the velocity of the red cells or in the diameter of the vessels in the normally irrigated cremaster muscles in the treated animals compared with the controls.

In contrast, as regards the cremaster muscle rendered ischemic, the mean diameter of the arterioles was improved in the treated animals compared with the controls. The velocity of the red cells was normalized by a treatment for 21 days.

In fact, in the treated animals, the velocity of the red cells and the blood flow rate measured 7 days after ligation show no significant difference from the values obtained in the cremaster not rendered ischemic. These results are obtained without modification of the arterial blood pressure.

These results indicate that chronic treatment with a compound of formula (I) improves the microcirculation and blood irrigation of regions rendered ischemic.

EXAMPLE 4: ACTIVITY OF THE COMPOUNDS OF FORMULA (I) ON THE TRANSMEMBRANE MOVEMENTS MACROMOLECULES AT MICROVASCULAR LEVEL IN MUSCLE RENDERED ISCHEMIC

The in vivo effects of the products of formula (I) on the transvascular movements of macromolecules induced by ischemia were studied.

The preparation involved rat cremaster muscle placed in a transparent chamber and perfused with bicarbonate buffer solution equilibrated with a 5%:95% $CO_2/N_2$ gaseous mixture so as to obtain a pH of 7.40.

Bovine serum albumin (fraction IV) labeled with fluorescein isothiocyanate (FITC-BSA) was injected as a macromolecular tracer (15 mg.kg$^{-1}$). Ischemia was produced for one hour with a clamp placed on the main artery of the cremaster muscle.

The clearance of FITC-BSA was calculated by the ratio of the extravasation per unit tissue weight to the plasma FITC-BSA concentration, this result being expressed as a percentage of the mean value obtained during a prior 20-minute control period.

The animals treated orally for 3 days with 1 mg.kg$^{-1}$ per day of a product of formula (I) show a higher macromolecular extravasation under the effect of bradykinin than that found in the control animals. These results demonstrate the inhibitory effect of a product of formula (I) on the angiotensin-converting enzyme present in the muscular microcirculatory system.

A treatment with a compound of formula (I) significantly reduces the increase in microvascular permeability observed in vivo as a result of one hour of total ischemia.

EXAMPLE 5: ACTIVITY OF THE COMPOUNDS OF FORMULA (I) WITH RESPECT TO THE ELASTIC PROPERTIES OF RAT AORTA

The impairment of the elastic properties of rat aorta was studied in three groups of Goldblatt rats.

Hypertensive rats were treated for five weeks with a product of formula (I) on the basis of 0.1 mg.kg$^{-1}$ and 0.01 mg.kg$^{-1}$; their aortae were studied after five weeks and compared with the aortae of rats which had not received any treatment.

Aortic fragments were suspended in organ chambers filled with modified Krebs Ringer bicarbonate solution. These fragments were treated with papaverine ($10^{-4}$ M) and sodium nitroprusside ($10^{-4}$ M) to suppress any interference due to the active tension developed by the smooth muscle. Aortic fragments from hypertensive rats developed a higher tension than that of the aortic fragments from normotensive rats subjected to identical stretching.

The treatment of sham-operated and normotensive rats with 0.1 mg.kg$^{-1}$ per day of the product of formula (I) did not give rise to significant differences from the controls, which were also sham-operated. The aortic fragments of hypertensive rats treated with 0.01 mg.kg$^{-1}$ per day of product of formula (I) developed a lower tension than that of the untreated animals.

The results of a test of this kind confirm the possibilities of using medicinal products obtained from compounds of formula (I) in disorders of the vascular wall.

EXAMPLE 6: EFFECTS OF A CHRONIC ADMINISTRATION NON-HYPOTENSIVE DOSES OF COMPOUNDS OF FORMULA (I) IN HYPERTENSIVE RATS

This study, carried out in a large number of rats, shows, in the first place, that the onset of hypertension resulting from the installation of a clip on the renal artery gives rise to a parallel and significant increase in the weight of the aorta (Goldblatt rat) (+21%).

The compounds of formula (I), administered at a dose of 0.1 mg.kg$^{-1}$ per day for 5 weeks in sham-operated rats, do not modify the blood pressure, but give rise to a significant decrease in the weight of the aorta ($-14\%$) of the treated rats in comparison with rats treated with placebo.

This test shows the important part played by the derivatives of formula (I), administered chronically, with respect to the properties of the vascular wall.

EXAMPLE 7: PHARMACEUTICAL COMPOSITION

Preparation formula for 1,000 tablets containing a 0.3 mg dose of active principle.

| | |
|---|---|
| (S)-2-{(S)-2-[(S)-1-Ethoxycarbonyl-3-phenylpropyl-amino]-1-oxopropyl}-3-carboxy-2-azabicyclo[2.2.2]-octane | 300 mg |
| Hydroxypropylcellulose | 2 g |
| Wheat starch | 10 g |
| Lactose | 100 g |
| Magnesium stearate | 3 g |
| Talc | 3 g |

What is claimed is:

1. A method for the treatment of arteritis including disorders of vision associated with arteritis,
   in a patient in need of the same, comprising the step of administering to said patient an amount of a 2-azabicyclo[2.2.2]octane compound of Formula I:

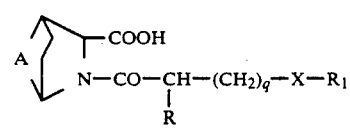

in which
A denotes dimethylene,
q is 0,
R denotes lower-alkyl ($C_1$-$C_4$) which can bear an amino group,
X denotes —NH—, and
$R_1$ denotes

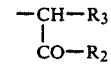

wherein
$R_2$ denotes hydroxyl or ($C_1$-$C_4$) lower-alkoxy,
$R_3$ denotes ($C_1$-$C_4$) alkyl or phenyl ($C_1$-$C_4$) alkyl
or a pharmaceutically-acceptable salt thereof with a therapeutically-compatible inorganic or organic base or with a therapeutically-compatible inorganic or organic acid,
which is effective for said purpose but essentially devoid of antihypertensive effect.

2. A method of claim 1 wherein the asymmetric carbon atoms in the compound of Formula I have the S configuration.

3. A method of claim 1, wherein, in the compound of Formula I, R=methyl and $R_3$=2-phenylethyl 4. A method of claim 3, wherein the daily dosage is not more than about 0.1 mg.kg$^{-1}$/day.

5. A method of claim 1, wherein the compound of Formula I is (S,S,S)-2-{2-[3-phenyl-1-(ethoxycarbonyl)-propylamino]-propionyl}-3-carboxy-2-azabicyclo[2.2.2]octane or a salt thereof with a pharmaceutically-acceptable inorganic or organic base or a pharmaceutically-acceptable inorganic or organic acid.

6. A method of claim 5, wherein the daily dosage is not more than about 0.1 mg.kg$^{-1}$/day.

* * * * *

UNITED STATES PATENT AND TRADEMARK OFFICE
CERTIFICATE OF CORRECTION

PATENT NO. : 5,021,425

DATED : Jun. 4, 1991

INVENTOR(S) : Bernard Teisseire

It is certified that error appears in the above-identified patent and that said Letters Patent is hereby corrected as shown below:

Title Page, [54], line 2; "AZABICYCLOI" should read
-- AZABICYCLO --.
Column 1, line 2; "AZABICYCLOI" should read -- AZABICYCLO --.
Column 1, line 8; "derivatives treatment" should read
-- derivatives for the treatment --.
Column 4, line 47; "MOVEMENTS MACROMOLECULES " should read
-- MOVEMENTS OF MACROMOLECULES --.
Column 5, approximately line 46; "ADMINISTRATION NON-" should
read -- ADMINISTRATION OF NON- --.

Signed and Sealed this

Twenty-seventh Day of October, 1992

Attest:

DOUGLAS B. COMER

*Attesting Officer*   *Acting Commissioner of Patents and Trademarks*